(12) United States Patent
Egerter

(10) Patent No.: US 11,992,635 B2
(45) Date of Patent: May 28, 2024

(54) MEDICAL BALLOON ASSEMBLY

(71) Applicant: MEDTRONIC VASCULAR, INC., Santa Rosa, CA (US)

(72) Inventor: Risa Tom Egerter, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 577 days.

(21) Appl. No.: 16/794,766

(22) Filed: Feb. 19, 2020

(65) Prior Publication Data
US 2020/0269023 A1 Aug. 27, 2020

Related U.S. Application Data

(60) Provisional application No. 62/810,195, filed on Feb. 25, 2019.

(51) Int. Cl.
*A61M 25/10* (2013.01)
*A61L 29/04* (2006.01)
(Continued)

(52) U.S. Cl.
CPC ....... *A61M 25/1029* (2013.01); *A61L 29/049* (2013.01); *A61L 29/06* (2013.01); *A61M 25/0045* (2013.01); *A61M 25/1006* (2013.01); *A61M 25/1025* (2013.01); *A61M 25/1034* (2013.01); *A61M 25/1036* (2013.01); *B29C 48/00* (2019.02); *A61M 2025/1031* (2013.01);
(Continued)

(58) Field of Classification Search
CPC ...... A61M 25/0069; A61M 2025/1093; A61M 25/1034; A61M 2025/1031; A61M 2025/1063
See application file for complete search history.

(56) References Cited

U.S. PATENT DOCUMENTS 5,108,416 A    4/1992 Ryan et al.
5,501,759 A    3/1996 Forman
(Continued)

FOREIGN PATENT DOCUMENTS

EP    1683540 A1    1/2006
EP    1683540 A1 *  7/2006    ............. A61F 2/958
(Continued)

OTHER PUBLICATIONS

International Search Report and Written Opinion dated Jun. 26, 2020 from related International Application No. PCT/US2020/019056, International Filing Date Feb. 20, 2020.
(Continued)

*Primary Examiner* — Kami A Bosworth
(74) *Attorney, Agent, or Firm* — Stinson LLP

(57) ABSTRACT

In one aspect, a medical balloon assembly includes a tip sleeve secured to the distal end portion of a balloon catheter that includes the distal neck of a balloon. The tip sleeve has at least an inner layer and an outer layer. The inner layer is formed from a bondable material that is directly bondable to the exterior of the distal neck portion of the balloon. The tip sleeve is bonded directly to the distal neck of the balloon. The outer layer is formed from a lubricious polymer. Such a medical balloon assembly is made by receiving the distal neck inside the proximal end portion of the tip sleeve and directly bonding the distal neck of the balloon to the inner layer of the tip sleeve.

16 Claims, 3 Drawing Sheets

(51) Int. Cl.
    *A61L 29/06* (2006.01)
    *A61M 25/00* (2006.01)
    *B29C 48/00* (2019.01)

(52) U.S. Cl.
    CPC ............ *A61M 2025/1056* (2013.01); *A61M 2025/1075* (2013.01); *A61M 2025/1093* (2013.01)

(56) References Cited

U.S. PATENT DOCUMENTS

| | | | |
|---|---|---|---|
| 6,139,525 | A | 10/2000 | Davis-Lemessy et al. |
| 6,221,467 | B1 | 4/2001 | Nazarova et al. |
| 6,837,897 | B2 | 1/2005 | Holman et al. |
| 8,690,905 | B2 | 4/2014 | Heidner et al. |
| 2002/0082549 | A1 | 6/2002 | Duchamp |
| 2005/0043712 | A1* | 2/2005 | Devens ............ A61M 25/0045 604/525 |
| 2006/0004399 | A1 | 1/2006 | van Ockenburg et al. |
| 2008/0262470 | A1* | 10/2008 | Lee .................. A61M 25/0069 604/509 |
| 2011/0172696 | A1 | 7/2011 | Jeffrey et al. |
| 2014/0276400 | A1 | 9/2014 | Le |

FOREIGN PATENT DOCUMENTS

| | | | |
|---|---|---|---|
| EP | 2029212 B1 * | 5/2012 | ........ A61M 25/0045 |
| WO | 1998007390 A1 | 2/1998 | |
| WO | WO-2012109468 A1 * | 8/2012 | ......... A61B 17/3207 |

OTHER PUBLICATIONS

Chinese First Office Action and Search Report for Application No. 202080014349.1, dated Feb. 6, 2023, 15 pages, China.

* cited by examiner

MEDICAL BALLOON ASSEMBLY

CROSS-REFERENCE TO RELATED APPLICATIONS

This application claims priority to U.S. Provisional Patent Application No. 62/810,195, entitled MEDICAL BALLOON ASSEMBLY and filed Feb. 25, 2019, which is hereby incorporated by reference in its entirety.

FIELD OF THE DISCLOSURE

This disclosure generally pertains to medical balloons and a medical balloon assembly.

BACKGROUND

Balloons mounted on the distal ends of catheters or other medical devices are widely used in medical treatment. For example, a medical balloon may be used to widen a vessel into which the catheter is inserted, open a blocked vessel and/or deliver a medical device (e.g., a stent) to a treatment location inside a body, among other uses. In use, the balloon is delivered to a treatment location by inserting the balloon in an uninflated configuration through a body lumen (e.g., a blood vessel). Balloons can be inserted through a body lumen by tracking the uninflated balloon through an introducer sheath and/or along a guidewire. Once the uninflated balloon has reached the treatment location, fluid is delivered into the balloon, thereby expanding the outer circumference of the balloon (i.e., the balloon is inflated). After treatment, the balloon is deflated and withdrawn from the patient's body. In some cases, the balloon may later be re-introduced into the same or another body lumen of the patient.

SUMMARY

In one aspect, a medical balloon assembly includes a tip sleeve secured to the distal end portion of a balloon catheter that includes the distal neck of a balloon. The tip sleeve has at least an inner layer and an outer layer. The inner layer is formed from a bondable material that is directly bondable to the exterior of the distal neck portion of the balloon. The tip sleeve is bonded directly to the distal neck of the balloon. The outer layer is formed from a lubricious polymer. Such a medical balloon assembly is made by receiving the distal neck inside the proximal end portion of the tip sleeve and directly bonding the distal neck of the balloon to the inner layer of the tip sleeve.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
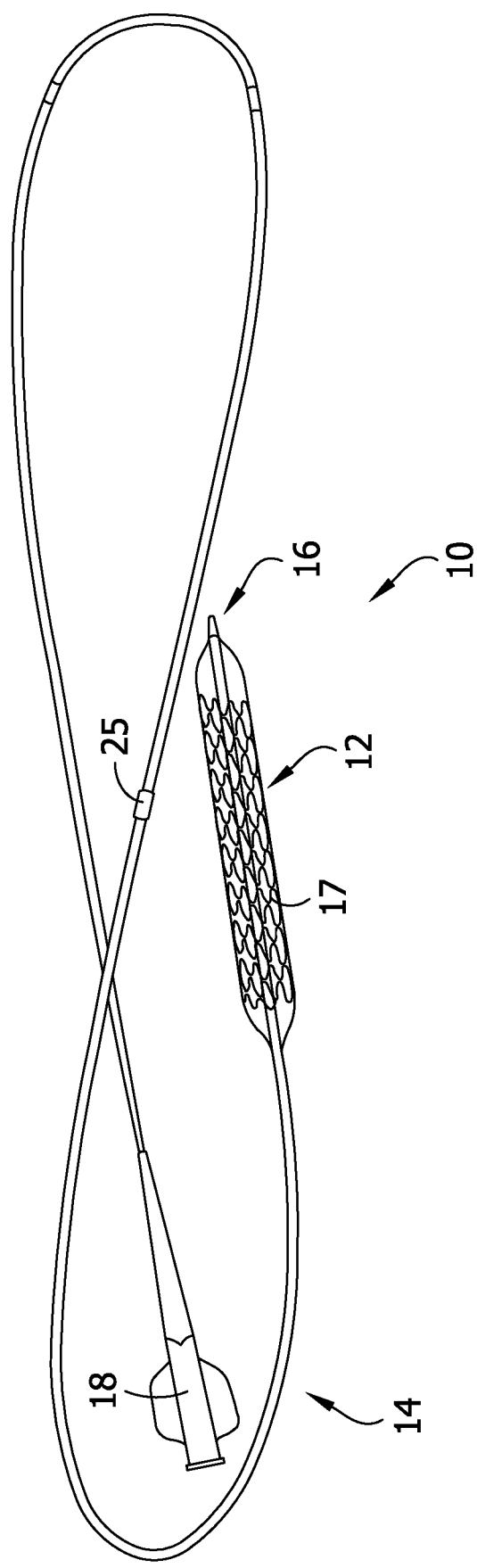
FIG. 1 is a perspective of a balloon catheter.
Figure 2:
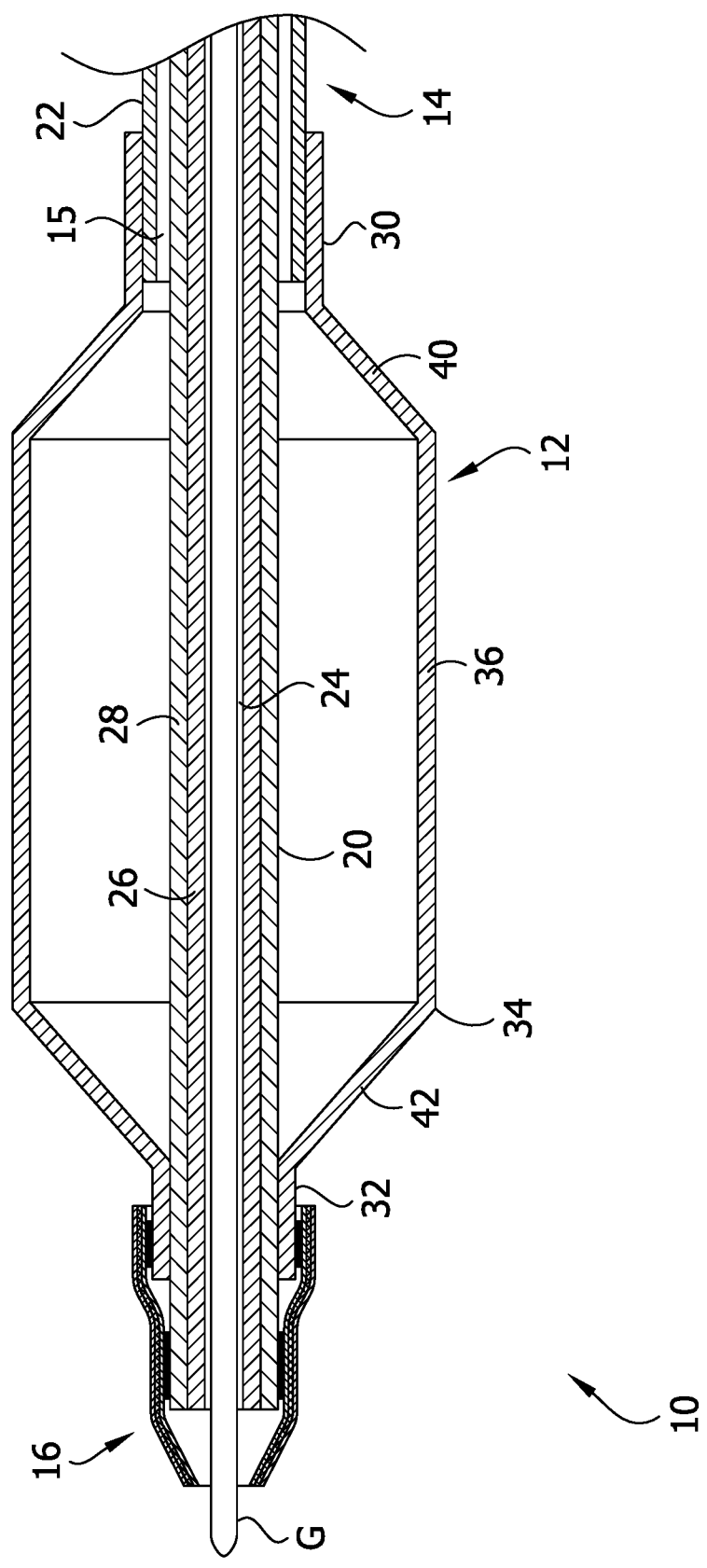
FIG. 2 is a fragmentary longitudinal cross-section of a distal end portion of the balloon catheter of FIG. 1 with a stent thereof removed.

Referring to FIGS. 1 and 2, one embodiment of a medical balloon assembly comprising a balloon catheter is generally indicated at reference number 10. In general, the balloon catheter 10 comprises a balloon, generally indicated at 12, and an inflation conduit, generally indicated at 14. The inflation conduit 14 defines an inflation lumen 15 and is fluidly coupled to the balloon 12 to deliver inflation fluid through the inflation lumen to the interior of the balloon. The medical balloon assembly 10 further comprises a tip sleeve, generally indicated at 16, secured to the distal end portion of the balloon 12. As will be explained in further detail below, the tip sleeve 16 is thought to enhance the deliverability of the medical balloon assembly 10 by reducing the force required for tracking the balloon catheter distally through a patient's anatomy.

Throughout this disclosure, a "medical balloon assembly" is used to mean a medical device that comprises a balloon and a tip sleeve, each constructed according to one or more teachings set forth in the present disclosure. The medical balloon assembly may comprise additional components and/or may be part of a larger assembly. That is, at a minimum, the medical balloon assembly has a balloon and a tip sleeve. In the illustrated embodiment, the medical balloon assembly 10 comprises a fully assembled balloon catheter that includes the balloon 12 and the tip sleeve 16, among other components. For example, the balloon catheter may also comprise a stent 17 (FIG. 1) received around the deflated balloon. It will be understood that a medical balloon assembly can comprise a subassembly of the balloon catheter. For example, in one or more embodiments, a medical balloon assembly comprises the balloon 12 and the tip sleeve 16 in a subassembly separate from the inflation conduit 14.

The illustrated inflation conduit 14 is part of an elongate catheter body of the illustrated balloon catheter. The inflation conduit 14 has a proximal end portion connected to an inflation fitting 18, a distal end portion secured to the balloon 12, and a length extending along an axis of the inflation conduit from the proximal end portion to the distal end portion. The inflation fitting 18 is configured to fluidly couple the inflation conduit 15 to a source of inflation fluid (not shown). In one or more embodiments, the inflation lumen 15 extends from the proximal end portion to the distal end portion to provide fluid communication between the source of inflation fluid and the interior of the balloon 12. As shown in FIG. 2, the illustrated inflation conduit 14 comprises an inner inflation tube, generally indicated at reference numeral 20, and an outer inflation tube 22. The inflation lumen 15 is located radially between the inner inflation tube 20 and the outer inflation tube 22. In other embodiments, the inflation conduit can have other configurations (e.g., the inflation conduit can comprise a single tube).

In the illustrated embodiment, the outer inflation tube 22 is configured to be fluidly coupled to a proximal end portion of the balloon 12. For example, in one or more embodiments, the outer inflation tube 22 is configured to be directly bonded to the proximal end portion of the balloon 12 to form a fluid seal between the outer inflation tube and the balloon. Throughout this disclosure "direct bond," "directly bonded," and "directly bondable" are used to indicate a bond (e.g., a fusion bond) between two parts or materials that requires no bonding structure (e.g., adhesive, a tie layer, etc.) interposed between the parts or materials. To facilitate a direct bond between the outer inflation tube 22 and the balloon 12, in one or more embodiments, at least contacting or coupling portions of the outer inflation tube and the balloon are formed from a polymer of the same type. For example, in one or more embodiments, the coupling portions the outer inflation tube 22 and the balloon 12 are formed from one of a polyether block amide (PEBA) and a nylon. In certain embodiments, the coupling portions of the outer inflation tube 22 and the balloon 12 are formed from the same material (e.g., the coupling portions of the outer inflation tube and the balloon are each formed from one of PEBAX® elastomer and nylon 12). Though the illustrated outer inflation tube 22 is directly bonded to the balloon 12, in other embodiments, the outer inflation tube could be fluidly coupled to the balloon in other ways.

In the illustrated embodiment, the inner inflation tube 20 functions as a guidewire tube defining a guidewire lumen 24. The guidewire lumen 24 is configured to slidably receive a guidewire G therein such that the balloon catheter 10 can be advanced along a body lumen by sliding along a preplaced guidewire. The inner inflation tube 20 has a distal end portion that is received in the distal end of the balloon 12 and protrudes distally from the distal end of the balloon. The distal end portion of the inner inflation tube 20 defines the distal end of the guidewire lumen 24. The guidewire G is configured to extend distally from the distal end of the inner inflation tube 20 during use. The guidewire lumen 24 extends from the distal end of the inner inflation tube 20 through a proximal end (not shown) of the inner inflation tube that is proximal of the proximal end of the balloon 12. Referring to FIG. 1, in the illustrated embodiment, the balloon catheter 10 comprises a rapid exchange catheter. In the rapid exchange balloon catheter 10, the inflation conduit 14 includes a rapid exchange joint 25. The guidewire tube 20 extends from the distal end portion that defines an opening through the distal end of the balloon 12 to a proximal end portion at the rapid exchange joint 25 that defines a lateral guidewire opening (not shown) through the outer inflation tube 22 at a location spaced apart between the proximal end of the balloon and the proximal end of the inflation conduit 14. In certain embodiments, the balloon catheter 10 comprises an over-the-wire catheter. In an over-the-wire balloon catheter, the proximal end of the guidewire lumen is located generally at the proximal end of the inflation conduit. In one or more embodiments, balloon catheters of other configurations (e.g., on-the-wire balloon catheters) can also be used.

In the illustrated embodiment, the inner inflation tube 20 (e.g., the guidewire tube) comprises a multilayer tube. But in one or more embodiments, the inner inflation tube can also have other configurations (e.g., comprise a monolithic tube formed from a single layer of material). The inner inflation tube 20 comprises a lubricious inner circumferential layer 26 and a bonding outer circumferential layer 28. In one or more embodiments, the inner inflation tube can also include one or more intermediate layers (not shown; e.g., a tie layer) located radially between the inner and outer circumferential layers 26, 28. Each of the inner and outer circumferential layers 26, 28 (as well as any intermediate layer) extends continuously along the length of the inner inflation tube 20. In certain embodiments, each of the circumferential layers 26, 28 of the inner inflation tube 20 are coextruded. The inner circumferential layer 26 defines the guidewire lumen 24 and is thus configured to slidably receive the guidewire G therein. In certain embodiments, the inner circumferential layer 26 is formed from a lubricious polymer. For example, in one or more embodiments, the inner circumferential layer is formed from a high density polyethylene (HDPE). Using a lubricious polymer for the inner circumferential layer 26 can lessen frictional forces between the guidewire G and the inner inflation tube 20 as the balloon catheter 10 slides along the guidewire. A lubricious coating can also be applied to the inner surface of the inner layer 26 in one or more embodiments.

The inner inflation tube 20 is configured to be sealingly connected to the distal end portion of the balloon 12. For example, in one or more embodiments, the inner inflation tube 20 is configured to be directly bonded to the distal end portion of the balloon 12 to form a fluid seal between the inner inflation tube and the balloon. To facilitate a direct bond between the inner inflation tube 20 and the balloon 12, in certain embodiments, at least the coupling portions of the inner inflation tube and the balloon are formed from a polymer of the same type. In the illustrated embodiment, the coupling portion of the inner inflation tube 20 is formed by the outer layer 28. Thus, in one or more embodiments, the outer layer 28 is formed from a bondable material that is directly bondable to the material forming the coupling portion of the balloon. In the illustrated embodiment, the outer layer 28 of the inner inflation tube 20 and the coupling portion of the balloon 12 are formed from one of a PEBA and a nylon. In certain embodiments, the outer layer 28 of the inner inflation tube 20 and the coupling portion of the balloon 12 are formed from the same material (e.g., the outer layer of the inner inflation tube and the balloon are each formed from one of PEBAX® elastomer and nylon 12). Though the inner inflation tube 20 is directly bonded to the balloon 12 in the illustrated embodiment, in other embodiments, the inner inflation tube could be sealingly coupled to the balloon in other ways.

In the illustrated embodiment, the balloon 12 comprises a single piece of monolithic material. For example, in one or more embodiments, the balloon 12 is formed from a bondable material, such as one of a PEBA and a nylon (e.g., one of PEBAX® elastomer and nylon 12). Accordingly, in one or more embodiments the balloon 12 is configured for being directly bonded to the outer inflation tube 22 and the outer layer 28 of the inner inflation tube 20. The balloon can also have other configurations. For example, in one or more embodiments, the balloon can comprise a multi-layer balloon (e.g., co-extruded, multilayer balloon) or have other arrangements of sections of discrete materials. In certain embodiments, when the balloon is formed from multiple materials, portions (e.g., layers) of the balloon that contact the inflation conduit and/or the tip sleeve are formed from bondable materials such that the components of the medical balloon assembly can be secured by direct bonds.

The balloon 12 comprises a proximal neck 30 defining the proximal end of the balloon, a distal neck 32 defining the distal end of the balloon, a length extending along an axis of the balloon from the proximal end to the distal end thereof, and an inflatable portion 34 extending along the length of the balloon between the proximal and distal necks. The distal end portion of the inner inflation tube 20 is received in the distal neck 32 such that the distal neck radially overlaps the distal end portion of the inner inflation tube. The distal end portion of the outer inflation tube 22 is likewise received in the proximal neck 30 such that the proximal neck radially overlaps the distal end portion of the outer inflation tube. In the illustrated embodiment, the proximal and distal necks 30, 32, are directly bonded to the outer inflation tube 22 and the inner inflation tube 20, respectively. Suitably, the direct bonds fluidly seal the interfaces between the balloon 12 and the inflation conduit 14 such that inflation fluid cannot escape the balloon through the interfaces. The balloon 12 may be attached to the inflation conduit 14 in other ways.

The inflatable portion 34 of the balloon 12 comprises a body 36, a proximal cone 40 extending between the proximal neck 30 and the body, and a distal cone 42 extending between the distal neck 32 and the body. When inflation fluid is delivered to the interior of the balloon 12 through the inflation conduit 14, the inflatable portion 34 is configured to radially expand from an uninflated configuration (not shown) to an inflated configuration (FIG. 1). In one or more embodiments, in the uninflated configuration of the balloon 12, the inflatable portion 34 comprises folds (e.g., wings) that are configured to wrap circumferentially around the balloon. The balloon can also have other arrangements in the uninflated configuration in certain embodiments. In one or more embodiments, the balloon 12 can be one of non-compliant, semi-compliant, and compliant in the inflated configuration. In the illustrated embodiment, the inflatable portion 34 of the balloon 12 has a generally cylindrical shape having conically tapered end segments in the inflated configuration. In one or more embodiments, the balloon has other shapes in the inflated configuration.

Figure 3:
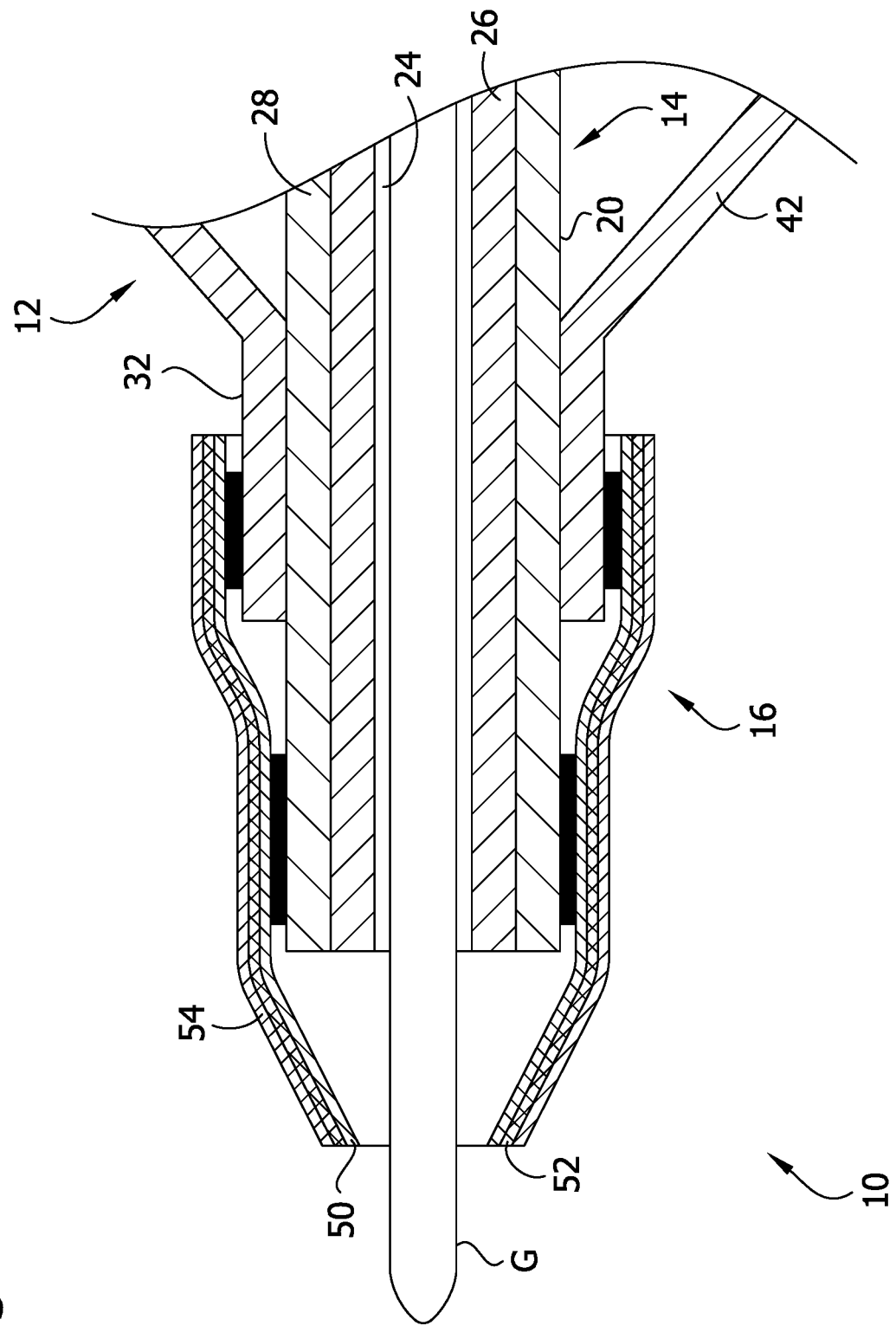
FIG. 3 is an enlarged view of the distal end portion of the catheter as shown in FIG. 2.

Referring to FIG. 3, the tip sleeve 16 has a proximal end portion, a distal end portion, and a length extending along an axis of the tip sleeve from the proximal end portion to the distal end portion. The tip sleeve 16 receives at least a portion of the distal neck 32 of the balloon 12 (broadly, the distal end portion of the balloon) therein such that the tip sleeve radially overlaps and circumferentially surrounds at least a portion of the distal neck. In the illustrated embodiment, the proximal end portion of the tip sleeve 16 receives the distal end portion of the distal neck 32 therein. In the illustrated embodiment, the tip sleeve 16 has a radially enlarged or flared proximal end portion that receives the distal neck 32 therein (e.g., the proximal end portion of the tip sleeve has a greater inner diameter and/or outer diameter than a middle portion and/or a distal end portion of the tip sleeve). In one or more embodiments, the tip sleeve could have a substantially constant inner diameter before being secured to a balloon. In these embodiments, the initial inner diameter is greater than the distal neck of the balloon such that the proximal end portion of the tip sleeve can receive the distal neck of the balloon and the distal end portion can be radially contracted (e.g., by lasers or heat shrink) to engage the inner inflation tube. Referring again to the illustrated embodiment, the proximal end of the tip sleeve 16 is spaced apart distally from the distal cone 42 (broadly, the inflatable portion 34). When the balloon 12 is in the uninflated configuration, the proximal end of the tip sleeve 16 is spaced apart distally from the folds of the balloon. In certain embodiments, the distal neck of the balloon could be received in another portion (e.g., the middle portion or the distal end portion) of the tip sleeve and/or a portion or the entirety of the distal cone (broadly, the inflatable portion of the balloon) can be received in the tip sleeve. The portion of the tip sleeve 16 that radially overlaps the balloon 12 is radially compressed against the balloon and generally conforms to the shape of the segment of the balloon against which it is radially compressed.

In the illustrated embodiment, the distal end portion of the tip sleeve 16 protrudes distally of the distal neck 32 of the balloon 12. The illustrated tip sleeve 16 receives the protruding distal end portion of the inner inflation tube 20 therein such that the tip sleeve radially overlaps the distal end portion of inner inflation tube. In the illustrated embodiment, the protruding distal end portion of the inner inflation tube 20 is radially overlapped by a middle portion of the tip sleeve 16 located along the length of the tip sleeve between the proximal and distal end portions thereof. In one or more embodiments, another portion of the tip sleeve (e.g., the proximal end portion or the distal end portion) radially overlaps the protruding portion of the inner inflation tube. The portion of the tip sleeve 16 that radially overlaps the protruding distal end portion of the inner inflation tube 20 is radially compressed against the inner inflation tube and generally conforms to the shape of the segment of the inner inflation tube against which it is radially compressed.

In the illustrated embodiment, the tip sleeve 16 has a transition section having an outer diameter and an inner diameter that tapers radially as it extends distally from the portion of the tip sleeve 16 that radially overlaps the balloon 12 to the portion of the tip sleeve that radially overlaps the protruding portion of the inner inflation tube 20. The tapered transition section of the tip sleeve 16 is thought to provide the leading end portion of the balloon catheter 10 with a smoother profile at the transition from the inner inflation tube 20 to the distal neck 30 than would be the case if the tip sleeve was omitted. The relatively smoothly tapered transition section of the tip sleeve 16 is thought to be less prone to becoming caught on obstacles (e.g., bends, lesions) in the body lumen as the balloon catheter 10 is advanced distally through the body lumen.

In the illustrated embodiment, the distal end portion of the tip sleeve 16 protrudes distally of the distal end of the inner inflation tube 20. The distal end portion of the tip sleeve 16 defines an opening through which the guidewire G is passable into the guidewire lumen 24. The outer diameter and the inner diameter of the tip sleeve 16 taper radially as the tip sleeve extends distally along the protruding distal end portion. Thus, the tip sleeve 16 has a tapered distal end portion that forms the distal end of the balloon catheter 10. The distal end portion of the tip sleeve 16 provides the balloon catheter 10 with a smoother and more tapered tip than would be the case if the blunt distal end of the inner inflation tube formed the tip of the balloon catheter if the tip sleeve was omitted. The tapered leading end provided by the tip sleeve 16 is thought to act as a conical wedge that facilitates guiding the balloon catheter 10 through narrow constrictions or other obstacles in a body lumen. Furthermore, in one or more embodiments, the protruding distal end portion of the tip sleeve 16 can be relatively soft (e.g., pliant, deformable), and therefore form an atraumatic tip at the distal end of the balloon catheter 10.

Although the tip sleeve 16 is described above as having a tapered, small-profile shape that facilitates guiding the balloon catheter 10 through a lumen, in certain embodiments, it may be desirable to increase the thickness of a portion or all of the tip sleeve to increase the strength of the tip sleeve. Accordingly, the thickness of the tip sleeve can be adjusted depending on the requirements of the application.

In one or more embodiments, the tip sleeve 16 has a color that contrasts with the color of the balloon. The colorized tip sleeve 16 is thought to enhance the visibility of the distal end of the balloon catheter 10, making it easier to load the balloon catheter distally onto the guidewire G. It will be appreciated that the tip sleeve can have generally the same color as the balloon in one or more embodiments.

Referring to FIG. 3, the illustrated tip sleeve 16 has a multilayer configuration. More specifically, the tip sleeve 16 comprises three concentric tube-shaped layers 50, 52, 54. In other embodiments, the tip sleeve can have other numbers and arrangements of layers. In one or more embodiments, the tip sleeve 16 is formed as a single extrusion such that the layers 50, 52, 54 comprise coextruded layers. The tip sleeve can also be formed in other ways in other embodiments. In the illustrated embodiment, the tip sleeve comprises an inner bonding layer 50, an intermediate tie layer 52, and an outer lubricious layer. As will be explained in further detail below, the inner bonding layer 50 is configured to facilitate securing the tip sleeve 16 in the balloon assembly 10 by one or more direct bonds, the outer lubricious layer 54 is configured to provide lubricity to the tip of the balloon catheter, and the inner tie layer 52 is configured to connect the inner bonding layer to the outer lubricious layer. As compared with providing lubricity by coating the tip of a balloon catheter with a lubricious coating, directly bonding the lubricious tip sleeve 16 to the balloon catheter 10 is thought to provide more durable lubricity and to facilitate more precise control of where lubricity is provided along the balloon catheter.

In general, the inner bonding layer 50 of the tip sleeve 16 is configured to be secured to at least one of the balloon 12 and the inner inflation tube 20 by a direct bond. For example, in one or more embodiments, the inner bonding layer 50 is configured to be directly bonded to each of the distal neck 32 of the balloon 12 and the protruding distal end portion of the inner inflation tube 20. Securing the tip sleeve 16 to the balloon 12 and/or the inner inflation tube 20 by a direct bond is thought to provide a robust connection that can withstand forces imparted on the balloon catheter 10 during use. In particular, the direct bonds between the tip sleeve 16 and the balloon 12 and/or the inner inflation tube 20 are thought to be capable of withstanding forces imparted on the balloon catheter 10 as the balloon catheter is delivered through a body lumen to a target site and withdrawn from the body lumen. Thus, it is contemplated that the illustrated balloon catheter 10 can be used repeatably (e.g., the balloon catheter can be advanced through a body lumen and withdrawn multiple times), with the tip sleeve 16 remaining secured in place.

To facilitate a direct bond between the inner tip sleeve 16 and the balloon 12, in one or more embodiments, the inner bonding layer 50 and the coupling portion of the balloon (e.g., at least an exterior portion of the distal neck 32) are formed from a polymer of the same type. Thus, in one or more embodiments, the inner bonding layer 50 of the tip sleeve 16 is formed from a bondable material that is directly bondable to the material forming the coupling portion of the balloon 12. For example, in one or more embodiments, the inner bonding layer 50 and the distal neck 32 of the balloon 12 are formed from one of a PEBA and a nylon. In certain embodiments, the inner bonding layer 50 and the distal neck 32 of the balloon 12 are formed from the same material (e.g., the inner bonding layer and distal neck are each formed from one of PEBAX® elastomer and nylon 12). The inner bonding layer of the tip sleeve and/or the distal neck of the balloon can also be formed from other materials in other embodiments.

To facilitate a direct bond between the inner tip sleeve 16 and the inner inflation tube 20, in one or more embodiments, the inner bonding layer 50 and the outer layer 28 of the inner inflation tube are formed from a polymer of the same type. Thus, in one or more embodiments, the inner bonding layer 50 is formed from a bondable material that is directly bondable to the outer layer 28 of the inner inflation tube 20. For example, in one or more embodiments, the inner bonding layer 50 and the outer layer 28 are formed from one of a PEBA and a nylon. In certain embodiments, the inner bonding layer 50 and the outer layer 28 are formed from the same material (e.g., the inner bonding layer and the outer layer of the inner inflation tube 20 are each formed from one of PEBAX® elastomer and nylon 12). The inner bonding layer of the tip sleeve and/or the outer layer of the inner inflation tube can also be formed from other materials in other embodiments.

In one or more embodiments, the outer lubricious layer 54 is formed from a lubricious polymer that is different than the material of the inner bonding layer 50 (e.g., the outer lubricious layer and the inner bonding layer comprise polymers of different types). For example, in certain embodiments, the outer lubricious layer 54 is formed from an HDPE, while the inner bonding layer 52 is formed from one of a PEBA and a nylon. The outer layer 54 can also be formed from other lubricious polymers in other embodiments (e.g., PTFE, a polymer comprising a lubricious additive). It will be appreciated that a lubricous polymer forming the outer lubricious layer 54 can have a relatively low coefficient of friction. Moreover, since the exterior of the tip sleeve 16 defines the leading end (e.g., the tip) of the balloon catheter 10 as the balloon catheter is advanced through a body lumen, the low coefficient of friction is thought to enhance deliverability of the balloon catheter. For example, the force required to push the balloon catheter 10 is thought to be less than the force required to push a similar balloon catheter that lacks the tip sleeve 16. In addition, because of the lubricious outer layer 54 of the tip sleeve 16, the balloon catheter 10 is thought to be capable of crossing smaller constrictions (e.g., lesions) in a body lumen than a similar balloon catheter that lacks the tip sleeve. In certain embodiments, the outer lubricious layer 54 can be coated with a lubricious coating. It is thought that using a lubricious coating in combination with a high-strength tip sleeve (e.g., a tip sleeve formed from a relatively hard or tough material and/or a tip sleeve of increased thickness) may enable the balloon catheter to pass through calcified lesions.

In the illustrated embodiment, the intermediate tie layer 52 is configured to connect the inner bonding layer 50 to the outer lubricious layer 54. Depending on the materials used for the inner bonding layer 50 and the outer lubricious layer 54, direct bonding between the inner and outer layers during coextrusion may not be possible. The tie layer 52 may, however, be directly bonded to each of the inner bonding layer 50 and the outer lubricious layer 54 to provide a strong connection between the inner and outer layers of the tip sleeve 16. In one or more embodiments, the intermediate tie layer 52 is formed from an acid-modified or anhydride-modified polyolefin resin such as one or more of a Plexar® resin, an Orevac® resin, a Bynel® resin or a Zelas™ resin. The intermediate tie layer can also be formed from other materials in certain embodiments. In one or more embodiments, the tie layer is omitted from the tip sleeve entirely such that the tip sleeve has a bilayer construction.

An exemplary method of making the balloon catheter 10 will now be described. Initially, a manufacturer extrudes a multilayer tube (for forming the tip sleeve 16) in a single extrusion. The manufacturer can cut a plurality of tip sleeves 16 from one coextruded multilayer tube. After the coextruded tip sleeve 16 is formed it can be secured to one or more additional components of a medical balloon assembly. As explained below, in certain embodiments the tip 16 sleeve can be secured to each of the balloon 12 and the inner inflation tube 20 at substantially the same time. In one or more embodiments, the tip sleeve 16 can also be secured separately to the balloon 12 to form a medical balloon assembly that is later coupled to the inflation conduit 14 to form the balloon catheter 10. The tip sleeve can also be secured to the balloon or inner inflation tube in other ways.

In one or more embodiments, the manufacturer assembles or is provided with a subassembly comprising the balloon 12, the inflation conduit 14, and a mandrel (not shown) received in the distal end portion of the guidewire lumen 24. The mandrel can be received in the guidewire lumen 24 such that it is radially overlapped by one or both of the distal neck 32 and the protruding distal end portion of the inner inflation tube 20. In the subassembly, the proximal neck 30 of the balloon 12 can be directly bonded to the outer inflation tube 22, but in certain embodiments, the distal neck 32 is not initially bonded to the inner inflation tube 20. The coextruded tip sleeve 16 is placed over the distal end portion of the subassembly such that the distal neck 32 of the balloon is received in the flared distal end portion of the tip sleeve, the protruding distal end portion of the inner inflation tube 20 is received in the middle portion of the tip sleeve, and the distal end portion of the tip sleeve protrudes distally from the distal end of the inner inflation tube.

The manufacturer places a heat shrink tube (not shown) over the tip sleeve 16 such that the heat shrink tube radially overlaps the tip sleeve along substantially the entire length of the tip sleeve. When the tip sleeve 16 and the heat shrink tube are in place on the distal end portion of the subassembly, the manufacturer then heats the heat shrink tube causing it to contract circumferentially. The contracted heat shrink tube compresses the tip sleeve 16 radially inward to conform the tip sleeve to the distal neck 32 of the balloon 12 and the protruding distal end portion of the inner inflation tube 20. The mandrel prevents the inner inflation tube 20 and the distal neck 32 from radially collapsing when the tip sleeve 16 is compressed.

With the heat shrink tube holding the tip sleeve 16 in place, the manufacturer directly bonds the tip sleeve to the distal neck 32 and the protruding distal end portion of the inner inflation tube 20. In one or more embodiments, the manufacturer welds (e.g., laser welds) the tip sleeve 16 to the distal neck 32 and the inner inflation tube 20 to form the direct bonds. In certain embodiments the manufacturer also directly bonds (e.g., welds, laser welds) the distal neck 32 of the balloon to the inner inflation tube 20 while the heat shrink tube is holding the tip sleeve in place. In one or more embodiments, after the direct bonds are formed, the heat shrink tube and the mandrel are removed from the assembled balloon catheter 10.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical balloon assembly, the medical balloon assembly comprising:
   a balloon comprising a distal end, a proximal end, and a length extending from the distal end of the balloon to the proximal end of the balloon, the balloon comprising a distal neck defining the distal end of the balloon and an inflatable portion proximal of the distal neck, at least an exterior portion of the distal neck being formed from a first bondable material;
   a tip sleeve having a proximal end, a distal end, and a length extending from the distal end of the tip sleeve to the proximal end of the tip sleeve, at least a first non-tapering longitudinal portion of the tip sleeve receiving at least a segment of the distal neck of the balloon therein such that the tip sleeve radially overlaps the distal neck, the tip sleeve comprising at least an inner layer and an outer layer, the inner layer comprising a second bondable material that is directly bondable to the first bondable material, the outer layer comprising a lubricious polymer, wherein the first non-tapering longitudinal portion of the tip sleeve is bonded directly to the distal neck of the balloon; and
   a guidewire tube defining a guidewire lumen, the guidewire tube being received in the distal neck of the balloon such that the distal neck radially overlaps the guidewire tube, the guidewire tube comprising a protruding distal end portion that protrudes distally from the distal neck of the balloon, wherein the protruding distal end portion of the guidewire tube is received inside the tip sleeve such that the tip sleeve radially overlaps the protruding distal end portion;
   wherein the tip sleeve has a second non-tapering longitudinal portion directly bonded to the protruding distal end portion of the guidewire tube,
   wherein the tip sleeve has a first tapered portion tapering from the first non-tapering longitudinal portion to the second non-tapering longitudinal portion of the tip sleeve, the first tapered portion being free from direct attachment to the protruding distal end portion of the guidewire tube, and
   wherein the tip sleeve has a second tapered portion tapering from the second non-tapering longitudinal portion toward the distal end of the tip sleeve, the second tapered portion being free from direct attachment to the protruding distal end portion of the guidewire tube.

2. A medical balloon assembly as set forth in claim 1, wherein the first bondable material comprises a polymer of a polymer type and the second bondable material comprises a polymer of the polymer type.

3. A medical balloon assembly as set forth in claim 2, wherein the polymer type is one of a polyether block amide and a nylon.

4. A medical balloon assembly as set forth in claim 1, wherein the first bondable material and the second bondable material are the same material.

5. A medical balloon assembly as set forth in claim 1, wherein the lubricious polymer comprises a high density polyethylene.

6. A medical balloon assembly as set forth in claim 1, wherein the tip sleeve further comprises an intermediate tie layer radially between the inner layer and the outer layer.

7. A medical balloon assembly as set forth in claim 6, wherein the intermediate tie layer is formed from a different material than either of the inner layer and the outer layer.

8. A medical balloon assembly as set forth in claim 6, wherein the intermediate tie layer is formed from a material that is directly bondable to the second bondable material and the lubricious polymer.

9. A medical balloon assembly as set forth in claim 6, wherein the inner layer, the intermediate tie layer, and the outer layer are coextruded.

10. A medical balloon assembly as set forth in claim 6, wherein the intermediate tie layer comprises one of an acid-modified polyolefin resin and an anhydride-modified polyolefin resin.

11. A medical balloon assembly as set forth in claim 1, wherein the inner layer and the outer layer of the tip sleeve are coextruded.

12. A medical balloon assembly as set forth in claim 1, wherein the distal end of the tip sleeve protrudes distally of the protruding distal end portion of the guidewire tube.

13. A method of making a medical balloon assembly as set forth in claim 1, the method comprising:
- receiving the distal neck of the balloon inside the proximal end of the tip sleeve; and
- directly bonding the distal neck of the balloon to the inner layer of the tip sleeve.

14. A method as set forth in claim 13, further comprising coextruding the inner layer and the outer layer of the tip sleeve in a single extrusion.

15. A method as set forth in claim 13, further comprising:
- after performing the step of receiving the distal neck of the balloon inside the proximal end of the tip sleeve, placing a heat shrink tube over the tip sleeve such that the heat shrink tube radially overlaps the tip sleeve and the distal neck of the balloon; and
- before performing the step of directly bonding the distal neck to the inner layer of the tip sleeve, heating the heat shrink tube to radially compress the proximal end of the tip sleeve against the distal neck of the balloon.

16. A method as set forth in claim 13, further comprising:
- receiving the protruding distal end portion of the guidewire tube that protrudes distally from the distal neck of the balloon inside the tip sleeve; and
- directly bonding the protruding distal end portion to the inner layer of the tip sleeve.

* * * * *